United States Patent [19]

Garrou

[11] 4,153,605

[45] May 8, 1979

[54] PROCESS FOR PREPARING BISPICOLYLAMINE

[75] Inventor: Philip E. Garrou, Holliston, Mass.

[73] Assignee: The Dow Chemical Company, Midland, Mich.

[21] Appl. No.: 910,242

[22] Filed: May 30, 1978

[51] Int. Cl.$^2$ ............................................. C07D 471/02
[52] U.S. Cl. .................................................... 546/264
[58] Field of Search ............................ 260/296 D, 690

[56] References Cited

U.S. PATENT DOCUMENTS

| 4,053,515 | 10/1977 | Drake | 260/690 X |
|---|---|---|---|
| 4,080,338 | 3/1978 | Garrou et al. | 260/296 D |

OTHER PUBLICATIONS

Klingsberg, Pyridine and Derivatives, Part Three, pp. 68–69 and 233–234, Interscience Publishers, NY (1962).

*Primary Examiner*—John D. Randolph
*Attorney, Agent, or Firm*—L. W. White; G. R. Plotecher

[57] ABSTRACT

Bispicolylamines are prepared by reacting (a) cyanopyridine with (b) hydrogen in the presence of a catalytic amount of (c) a palladium on α-alumina catalyst. The reaction is normally conducted under autogeneous or superatmospheric pressure at a temperature of from about 20° C. to about 75° C. in a lower alkanol (e.g., isopropanol) as the reaction medium.

8 Claims, No Drawings

PROCESS FOR PREPARING BISPICOLYLAMINE

BACKGROUND OF THE INVENTION

1. Field of the Invention

This is a new process for making bispicolylamine from cyanopyridines and hydrogen. Palladium on α-alumina is used as the catalyst.

2. Prior Art

Volkova et al. teach that cyanopyridines are hydrogenated in the presence of palladium (or palladium on carbon) to form the corresponding picolylamines (i.e., aminomethylpyridines). See Volkova et al.: *Chemical Abstracts*, 79: 42296n; 80: 120705q; 81: 49570x; 83: 28065n; and 83: 113388q. Matsumoto et al. (*Chemical Abstracts*, 82: 156097r) teach that 2,6-biscyanopyridines are hydrogenated to form the corresponding 2,6-bis-(aminomethyl)pyridines as the trihydrochloride salts when the reaction is conducted over palladium on carbon using hydrochloric acid/methanol as the hydrogenation medium. These references indicate that palladium and palladium on carbon are very effective catalysts in the reaction and produce the corresponding picolylamines selectively.

Garrou and Hartwell teach in U.S. Pat. No. 4,080,338 that bispicolylamines are prepared by reacting (a) cyanopyridine with (b) hydrogen in the presence of a catalytic amount of (c) a palladium or carbon catalyst which has been preconditioned by contact with a reacting mixture of (a) and (b) for a time sufficient to cause said catalyst to preferentially produce bispicolylamine. The reaction is normally conducted under autogenous or superatmospheric pressure at a temperature of from about 20° C. to about 75° C. in a lower alkanol (e.g., methanol) as the reaction medium.

SUMMARY OF THE INVENTION

I have discovered a new process for preparing bispicolylamines which comprises reacting by contacting under autogenous or superatmospheric pressure (a) a cyanopyridine with (b) hydrogen in the presence of a catalytic amount of (c) a palladium on α-alumina catalyst.

DETAILED DESCRIPTION OF THE INVENTION

The instant process is represented by the following equation:

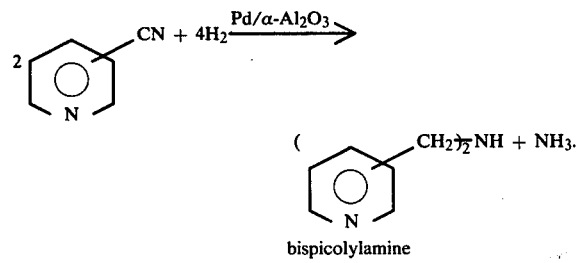

bispicolylamine

The reaction is conducted by efficiently blending the reactants and catalyst in a suitable reaction vessel (e.g., a trickle bed reactor) under autogenous or superatmospheric pressure. The reaction is exothermic and is preferably conducted in the presence of a liquid hydrogenation reaction medium. The lower alkanols of from 1 to 4 carbon atoms (e.g., methanol, ethanol, isopropanol, butanol, etc.) are normally suitable and ispropanol or t-butanol are preferred reaction mediums.

The reaction temperature and pressure are each independently variable and may be adjusted to convenience. Preferred rates of reaction, however, have been observed at temperatures in the range of from about 20° C. to about 100° C. (preferably from about 70° C. to about 90° C.). Preferred pressures range from autogenous up to about 400 psig. Such superatmospheric pressures are normally achieved by using excess hydrogen. This excess positive pressure of hydrogen tends to maximize conversion of the cyanopyridine reactant and maximize product yield.

The reactants in this process are, of course, well known. Any one of the three position isomers of cyanopyridine, or a mixture thereof, can be used in the instant process but 2-cyanopyridine is the most preferred reactant. Hydrogen is a gas and is normally sparged into the reaction mixture in substantial excess, as noted above.

The catalyst used herein is palladium supported on α-alumina, normally in the form of pellets. There are many commercial sources for palladium on α-alumina catalysts and such commercial catalysts are suitable for use herein. Alternatively, however, the catalyst can be prepared in situ by adding a soluble palladium salt along with α-alumina to the reaction medium in which case the catalyst is generated in situ. The instant catalyst can be used repeatedly to effect high conversion of the reactants. After repeated usage, however, the catalytic activity tends to decrease and the reaction temperature and/or pressure are normally adjusted upward to off-set this decrease and maintain the high degree of conversion.

The process can be conducted batchwise or continuously. A continuous process using, for example, a trickle bed reactor is convenient and economically preferred.

Experimental

The following experiments further illustrate the invention.

EXAMPLES 1-2

A series of reactions was conducted in a laboratory scale trickle bed reactor vessel containing 50 g of 0.5 weight percent palladium supported on α-alumina (as ⅛ inch tablets). The reaction vessel was pressurized to 350 pounds per square inch gauge with hydrogen and preheated to a temperature of 80° C. The liquid 2-cyanopyridine dissolved in methanol was then added dropwise onto the surface of the heated catalyst and leached through the catalyst bed for a total contact time of about 13 minutes. The liquid reaction product passing from the bottom of the catalyst bed in the reactor was collected and recirculated repeatedly into and through the catalyst bed under the same conditions. At the end of 6 hours, the conversion was 84 percent of theory, based on the 2-cyanopyridine charged. The product analyzed as 67 weight percent bispicolylamine, 30 weight percent picolylamine and 3 weight percent picolylamidine. At the end of 12 hours reaction time, the conversion was 98 percent of theory and the product analysed as 68 weight percent bispicolylamine, 28 weight percent picolylamine and 4 percent of the picolylamidine. In these experiments, the initial charge was 12 g of 2-cyanopyridine dissolved in 48 ml of methanol.

EXAMPLE 3

Using the above procedure except operating at atmospheric pressure using a positive flow of hydrogen gas at 8 cubic feet of hydrogen (standard temperature and pressure) through the system during the course of the reaction, the product showed conversion to be 98 percent complete at the end of 5 hours of reaction time and comprised 73 weight percent bispicolylamine, 21 weight percent picolylamine and 3 weight percent picolylamidine. The remaining products were not identified.

The products from the above examples were analyzed by gas phase chromatography using biphenyl as an internal standard. In comparative experiments under essentially identical conditions except that the catalyst was replaced with an equal amount of a palladium catalyst where the palladium was supported on gamma-alumina instead of α-alumina, the product mix was altered substantially with increasing amounts of picolylamine and decreasing amounts of bispicolylamine. The conversion rates were about the same.

In other experiments conducted in a rocking bomb, the effect of solvent was studied. Preliminary indications were that isopropanol and t-butanol were more effective solvents than methanol in reducing the amount of picolylamidine formed during the course of the reaction.

What is claimed is:

1. The process for preparing bispicolylamine comprising reacting by contacting with thorough mixing under autogenous or superatmospheric pressure (a) a cyanopyridine with (b) hydrogen in the presence of a catalytic amount of (c) a palladium on α-alumina catalyst.

2. The process defined by claim 1 wherein the reaction temperature is from about 20° C. to about 100° C.

3. The process defined by claim 1 wherein said reaction is conducted in a lower alkanol of from 1 to 4 carbon atoms.

4. The process defined by claim 3 wherein said lower alkanol is isopropanol or t-butanol.

5. The process defined by claim 1 wherein said process is conducted under a pressure of from autogenous up to about 400 psig.

6. The process defined by claim 5 wherein said pressure is due at least in significant part to excess hydrogen.

7. The process defined by claim 1 wherein (a) is 2-cyanopyridine.

8. The process defined by claim 7 wherein the reaction temperature is from about 70° C. to about 90° C., the reaction pressure is from autogenous up to about 400 psig and is the result of excess hydrogen, and wherein the reaction is conducted in a trickle bed reactor using methanol as the liquid reaction hydrogenating medium.

* * * * *